(12) United States Patent
Jaroszeski et al.

(10) Patent No.: US 8,017,368 B2
(45) Date of Patent: Sep. 13, 2011

(54) MOLECULAR DELIVERY TO CELLS USING ASPIRIN-RELATED COMPOUNDS

(75) Inventors: Mark J. Jaroszeski, Wesley Chapel, FL (US); Jennifer Langham, New Port Richey, FL (US); Richard Heller, Temple Terrace, FL (US); Richard Gilbert, Tampa, FL (US)

(73) Assignee: University of South Florida, Tampa, FL (US)

( * ) Notice: Subject to any disclaimer, the term of this patent is extended or adjusted under 35 U.S.C. 154(b) by 423 days.

(21) Appl. No.: 11/551,519

(22) Filed: Oct. 20, 2006

(65) Prior Publication Data

US 2007/0122908 A1    May 31, 2007

Related U.S. Application Data

(60) Provisional application No. 60/728,598, filed on Oct. 20, 2005.

(51) Int. Cl.
*C12N 13/00*    (2006.01)
*A61K 31/616*    (2006.01)

(52) U.S. Cl. .................................. 435/173.6; 514/165

(58) Field of Classification Search .................. None
See application file for complete search history.

(56) References Cited

U.S. PATENT DOCUMENTS

| | | | | |
|---|---|---|---|---|
| 3,670,085 | A * | 6/1972 | Pryor et al. | 514/368 |
| 4,440,762 | A * | 4/1984 | Rainsford et al. | 514/161 |
| 4,554,164 | A * | 11/1985 | DeYoung | 514/649 |
| 4,684,638 | A * | 8/1987 | Nagy et al. | 514/185 |
| 5,922,347 | A * | 7/1999 | Hausler et al. | 424/441 |
| 5,952,300 | A * | 9/1999 | Nerurkar et al. | 514/11 |
| 2003/0044985 | A1 | 3/2003 | Jaroszeski et al. | |
| 2004/0193097 | A1 | 9/2004 | Hofmann et al. | |
| 2005/0036952 | A1 | 2/2005 | Brucker | |
| 2005/0054969 | A1 | 3/2005 | Hoff et al. | |
| 2005/0170510 | A1 | 8/2005 | Huang et al. | |

* cited by examiner

*Primary Examiner* — Jim Ketter
(74) *Attorney, Agent, or Firm* — Michele L. Lawson; Smith & Hopen, P.A.

(57) ABSTRACT

The present invention provides for a system and method whereby aspirin and acetic acid help to permeabilize cell membranes to allow exogenous molecules to gain access to the cell interior. As such, the present invention provides a low cost drug and gene delivery tool that can be applied in combination with other molecular delivery methods.

19 Claims, 9 Drawing Sheets

MOLECULAR DELIVERY TO CELLS USING ASPIRIN-RELATED COMPOUNDS

CROSS REFERENCE TO RELATED APPLICATIONS

This application claims priority to currently U.S. Provisional Patent Application No. 60/728,598, entitled, "Aspirin and Acetic Acid for Molecular Delivery to Cells and Adjuvants for Molecular Delivery Methods", filed Oct. 20, 2005, the contents of which are herein incorporated by reference.

FIELD OF INVENTION

This invention relates to molecular delivery across a lipid bilayer. More specifically, this invention relates the use of acetylsalicyclic acid and acetic acid to enhance the delivery of target molecules across the membrane of a cell.

BACKGROUND OF THE INVENTION

The cell membrane is composed of a lipid bilayer having integral proteins and forms the outer-most layer of a cell. One crucial feature of the membrane is its selective permeability. The ability of various compounds and molecules to enter and exit the cell depends upon the size, charge and other chemical properties of the molecule. If a particle is too large, or its properties incompatible with diffusion across the membrane, the particle must enter through another route, such as a protein channel or the molecule could enter through endocytosis. These alternative routes nevertheless remain as significant limitations to entry.

A number of methods have been developed to facilitate the delivery of compounds across the cell membrane and into the cell. Among the chemical methods, calcium phosphate has been used for many years to introduce DNA into a cell. In performing the procedure, a precipitate of calcium phosphate is formed, which binds to the DNA in the precipitate solution. When a suspension of the solution is added to the cells to be transfected, the cells take up the precipitate, and with it the bound nucleic acid. Liposome-based transfection has emerged in recent years as a widely practiced method of delivering foreign compounds to the interior of a cell. Liposomes are spherical vesicles that can be used to deliver compounds, such as drugs or nucleic acids, to the interior of a cell. In delivering the compound, the liposome fuses with cell membrane, allowing the content of the vesicle to gain access to the cell's interior.

An additional technique for delivering molecules to the interior of a cell is electroporation. Electroporation is performed by exposing the cells to an electric potential that traverses the cell membrane. While its mechanism is not fully understood, electroporation is believed to involve the breakdown of the cell membrane lipid bilayer leading to the formation of transient or permanent pores in the membrane that permit the chemical species to enter the cell by diffusion. The electric potential is typically applied in pulses, and whether the pore formation is reversible or irreversible depends on such parameters as the amplitude, length, shape and repetition rate of the pulses, in addition to the type and development stage of the cell. Electroporation has many advantages, including simplicity and effectiveness across a wide variety of cells. Additionally, it can be used in conjunction with other techniques to improve the efficiency of those techniques.

SUMMARY OF INVENTION

The present invention provides for a system and method whereby aspirin and acetic acid help to permeabilize cell membranes to allow exogenous molecules to gain access to the cell interior. As such, the present invention provides a low cost drug and gene delivery tool that can be applied in combination with other molecular delivery methods.

In a first aspect the present invention provides a method of delivery of a desired substance across a cell membrane comprising contacting the membrane with a solution comprising the desired substance and acetylsalicyclic acid. In an advantageous embodiment the method may further include the step of applying an electric field to the contacted membrane to electroporate the membrane. In still further advantageous embodiments the concentration of acetylsalicyclic acid is greater than 5 mM. In a particularly advantageous embodiment the concentration of acetylsalicyclic acid is about 10 mM. In further advantageous embodiments the applied electric field is between about 500 V/cm and about 1000 V/cm.

In a second aspect the present invention provides a method of delivery of a desired substance across a cell membrane comprising the step of contacting the membrane with a solution comprising the desired substance and acetic acid. In an advantageous embodiment the method may further include the step of applying an electric field to the contacted membrane to electroporate the membrane. In still further advantageous embodiments the concentration of acetylsalicyclic acid is greater than 5 mM. In a particularly advantageous embodiment the concentration of acetylsalicyclic acid is about 10 mM. In further advantageous embodiments the applied electric field is between about 500 V/cm and about 1000 V/cm.

In a third aspect the present invention provides a method of permeabilizing a cell membrane to facilitate entry of a desired molecule into the cell comprising the step of contacting the cell with a solution comprising the desired molecule and a permeabilizing agent selected from the group consisting of acetylsalicyclic acid and acetic acid. In an advantageous embodiment the method may further include the step of applying an electric field to the contacted membrane to electroporate the membrane. In further advantageous embodiments the applied electric field is between about 500 V/cm and about 1000 V/cm. In still further advantageous embodiments the electric field is generated using short electrical pulses.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention provides for a system and method whereby aspirin and acetic acid help to permeabilize cell membranes to allow exogenous molecules to gain access to the cell interior. As such, the present invention provides a low cost drug and gene delivery tool that can be applied in combination with other molecular delivery methods.

As used herein the term "substance" is meant to refer to an element, charged species or compound, such as chemicals, drugs, proteins, and nucleic acids.

The invention is described below in examples which are intended to further describe the invention without limitation to its scope.

Example 1

Effects of Salicylic Acid on Calcein Delivered by Electroporation

Figure 6:
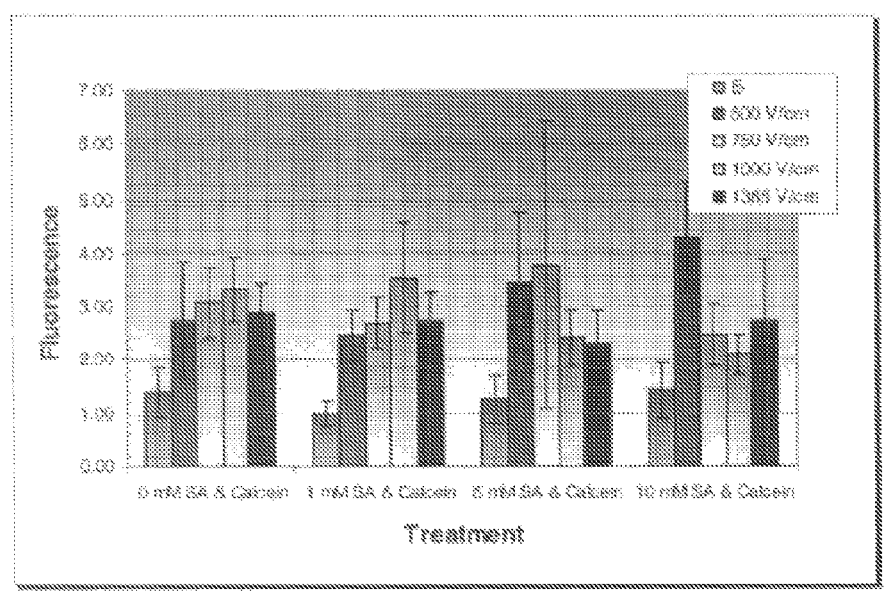
FIG. 6 is a graph illustrating the experimental results of the electroporated delivery with salicylic acid in accordance with the present invention.

The effects of salicylic acid ("SA") on the delivery of calcein to B16-F10 cells using electroporation was studied. Three identical experiments were carried out. FIG. 6 shows mean spectrofluorometric data for these experiments. All cells were exposed to 120 μM calcein. In addition, cells in some samples were exposed to one of three different concentrations of salicyclic acid (1 mM, 5 mM, or 10 mM) with pH values of 6.70, 6.32, and 3.85, respectively. Pulses with one of four different field strengths were also applied (500, 750, 1000, or 1385 V/cm) to certain samples. Salicyclic acid concentration and field strength were experimental variables; however, some cells were not exposed to applied fields or salicyclic acid for comparison/control purposes.

The results demonstrated that when cells were exposed to calcein and the three concentrations of SA (no applied electric field), salicyclic acid did not augment the delivery when compared to samples exposed to calcein alone. Overall, the data for samples treated with calcein and either 1, 5, or 10 mM salicyclic acid and electrical pulses were not significantly higher in fluorescent magnitude than any of the samples that were treated with calcein and pulses (no salicyclic acid).

Example 2

Effects of Acetylsalicylic Acid on Calcein Delivered by Electroporation

Figure 7:
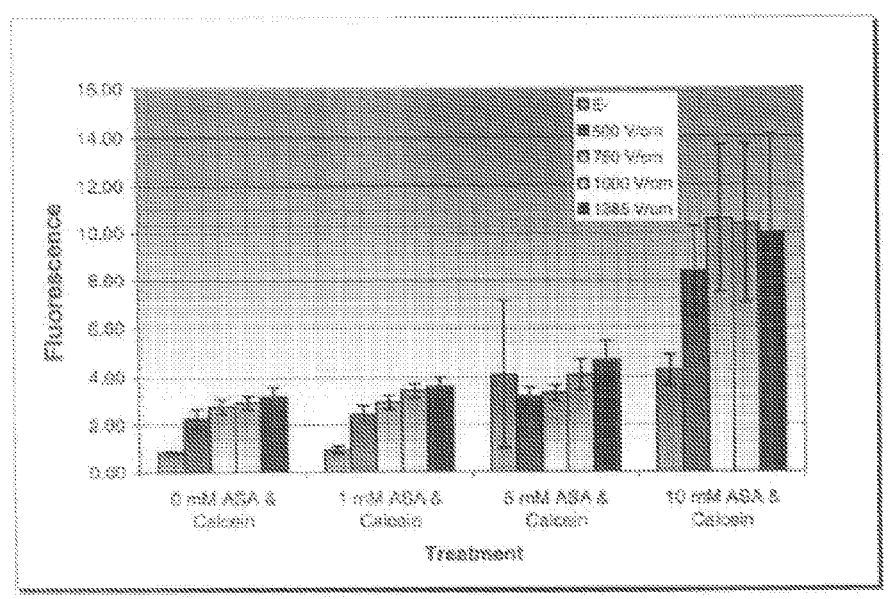
FIG. 7 is a graph illustrating the experimental results of the electroporated delivery with acetylsalicyclic acid in accordance with the present invention.

Delivery of calcein using aspirin (acetylsalicylic acid or "ASA") was studied. The treatments were similar to those in the previous section in that three concentrations of aspirin were used (1 mMl. 5 mM, or 10 mM) with pH values of 6.39, 5.40, and 4.40, respectively. The same range of pulsing conditions was used and the variables were identical for the sample treatment. FIG. 7 shows the mean data from three replicate experiments.

The data indicates that exposure to 1 mM or 5 mM ASA (alone) did not result in a significant increase in fluorescence magnitude when compared to the treatment of 120 M calcein alone (no ASA). In addition, samples treated with 1 and 5 mM ASA that were also exposed to electric fields had mean fluorescence magnitude that were not significantly different from those samples that were exposed to electric fields alone (no ASA). In contrast, samples that were exposed to calcein in 10 mM ASA (no pulses) had an average fluorescent magnitude of 4.28 (SEM=0.63) and samples that were exposed to calcein (no ASA or pulses) had mean fluorescent magnitude 0.83 (SEM=0.05). This 5-fold increase in internalized calcein that resulted from exposure to 10 mM ASA was statistically significant when compared to the control sample ($p<0.0001$). FIG. 7 also demonstrates that 10 mM ASA assisted in the delivery of calcein at each of the four electric fields. As the applied field was increased, the fluorescence remained at an elevated magnitude relative to samples that were exposed to 10 mM ASA (alone) and to samples that were exposed to the same electric fields alone. At 500 V/cm (and 10 mM ASA), there was a 3.7-fold increase in fluorescence magnitude relative to samples treated with calcein at 500 V/cm (no ASA). These same increases at 750, 1000, and 1385 V/cm were 3.82, 3.57, and 3.18-fold, respectively. The mean data with samples treated at each field were significantly different from analogous samples that did not include ASA. The p-values of these comparisons were <0.0001(500 V/cm), 0.0011(750 V/cm), 0.0014(1000 V/cm), and 0.0066 (1385 V/cm). Therefore, these data clearly show that 10 mM ASA alone can augment calcein delivery alone to the exterior of cells and also enhance delivery as a result of electroporation.

Example 3

Effects of Acetic Acid on Calcein Delivered by Electroporation

Calcein delivery by electroporation using acetic acid ("AA") as an effector was studied. The set of 3 replicate experiments included three concentrations of AA, each with a different pH (4.40, 5.36, or 6.42). The pH values of the three solutions of acetic acid were matched to those of ASA for the purpose of determining if AA is the derivative in ASA that enhances the delivery of calcein. The three concentrations of the AA solutions in PBS were similar, which was about 0.15%, and varied slightly in order to establish the desired pH value. In addition, one of three electric field strengths were applied to cells (500, 750, or 1000 V/cm). Some cells were not exposed to applied fields or any concentration of AA for purposes of comparison and control.

Figure 8:
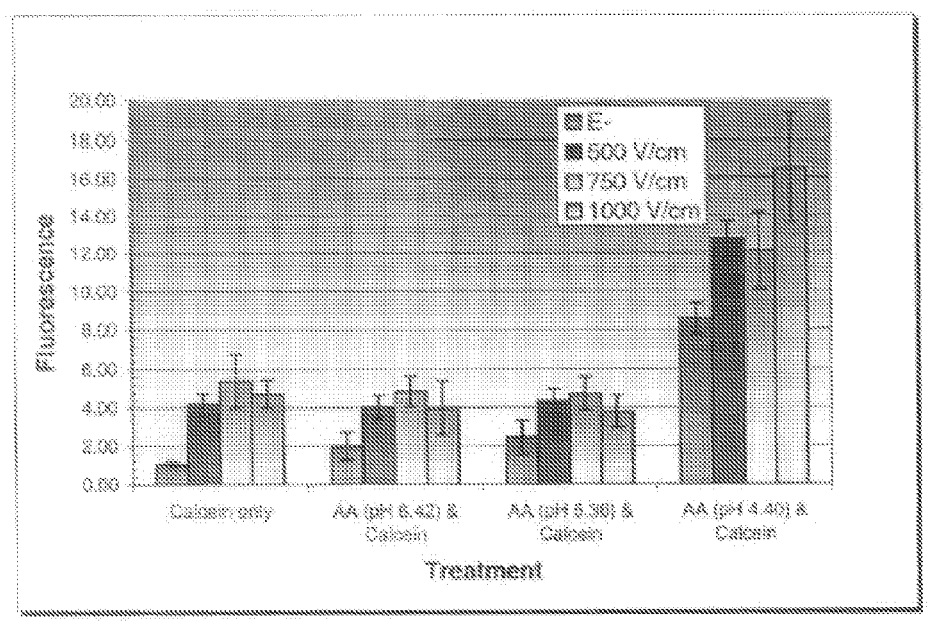
FIG. 8 is a graph illustrating the experimental results of the electroporated delivery with acetic acid in accordance with the present invention.

Samples treated with acetic acid failed to show a significant increase in fluorescence magnitude at higher pH (5.36 or 6.42) regardless of whether or not pulses were applied, when compared to samples not exposed to AA. However, FIG. 8 shows that acetic acid had a tremendous effect on the delivery of calcein, using a low pH solution (pH 4.40). The data for samples treated with AA alone (no pulses with a mean fluorescence magnitude of 1.04) was significantly different in mean fluorescence when compared to control samples that were not treated with AA or pulses (mean fluorescence magnitude of 8.57). This was an 8.2-fold increase. When electric fields were used in combination with the lowest pH solution of AA, fluorescent data was even higher than when this concentration of AA was used alone (no pulses).

The data for samples treated with AA and electrical pulses was significantly higher than any of the samples that were treated with calcein and pulses (no AA). At the lowest applied field, 500 V/cm, acetic acid augmented the resulting fluorescence magnitude by 3-fold. The mean fluorescence magnitudes were 12.77 for samples treated with AA (pH 4.40) and 4.19 for the samples that were not exposed to AA. This difference was significant (p<0.0001). For the 750 V/cm samples, this same increase was 2.25-fold and was statistically significant (p= 0.0002). Similarly, there was a 3.5-fold increase for the 1000 V/cm samples. This increase was also significant (p<0.0001).

As a result of this data, a low pH (4.40) solution of acetic acid is clearly a candidate to augment calcein for optimal E.P. delivery of calcein in B16F10 cells at any of the three electric fields, though it is often desired to apply lower field strengths to minimize the possibility of cellular damage.

Example 4

Membrane Recovery

Acetic acid was chosen for further investigation of the effects of treatment on cell membranes. It is desirable to achieve intact cell membranes following delivery methodology. The trypan blue test was used to determine membrane integrity. Trypan blue dye will only penetrate into cells that have porous membranes. The electric field strength of 750 V/cm was applied to triplicate wells containing PBS alone as well as acetic acid (pH 4.40) alone. In addition, for comparison, individual treatments of PBS and acetic acid (pH 4.40) without electrical pulses were investigated. The protocol used was similar to the methods described for the delivery of calcein. After one hour of exposure at 37° the cells were washed three times with 500 µl aliquots of PBS. Liquid from the last wash was carefully aspirated, and then filled with 500 µl of growth media.

Figure 9:
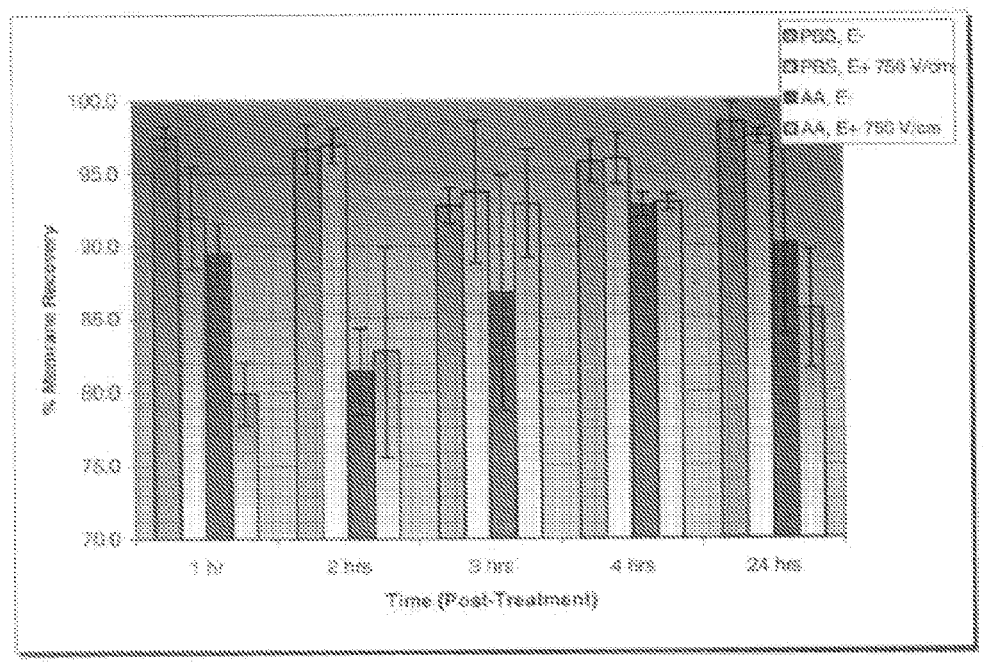
FIG. 9 is a graphical illustration of the membrane recovery of cells after exposure in accordance with the present invention.

FIG. 9 illustrates the time duration of membrane recovery after exposure. Treatments with PBS alone (no pulses) and with 750 V/cm applied electric field yielded between 90-100% membrane recovery during the 24 hours of observation. However, acetic acid alone had a greater impact on the recovery of the cells, ranging from an average of 80-95% membrane integrity. At a time of 1 hour post-treatment for samples treated with acetic acid at 750 V/cm, there was a 17% decline in the number of cells with intact membranes, implying that some of the cells either did not survive after exposure or were permeabilized. The number of cells that excluded the trypan blue dye then increased as the hours proceeded to a value of 86% after 24 hours. 90% of the cells exposed to AA alone had intact membranes 24 hours after treatment.

Observations

Both aspirin and acetic acid, when administered alone, showed the ability to augment the entry of nonpermeant calcein into cells. The addition of electroporation to treatment with acetic acid or aspirin led to further increases in internalized calcein. Cells recovered from the treatment to have intact membranes within several hours.

Materials and Methods

Cell Preparation Cell Line and Growth:

B16-F10 mouse melanoma cells (ATCC#:CRL-6475) were obtained and grown in McCoy's Media (Cellgro Mediatech, Inc., Herndon. VA), adjusted to contain 10% fetal bovine serum (Cellgro Mediatech, Inc.) and (25 mg) gentamicin 50 mg/mL (Mediatech, Inc.) and were incubated in 5% $CO_2$ at 37° C. Serum was essential for many reasons. It provided hormonal factors that stimulated cell growth and function. It also contains essential proteins, amino acids, minerals, and lipids. Gentamicin is an antibiotic used as a preventative measure to help reduce microbial growth and contamination.

Figure 1:
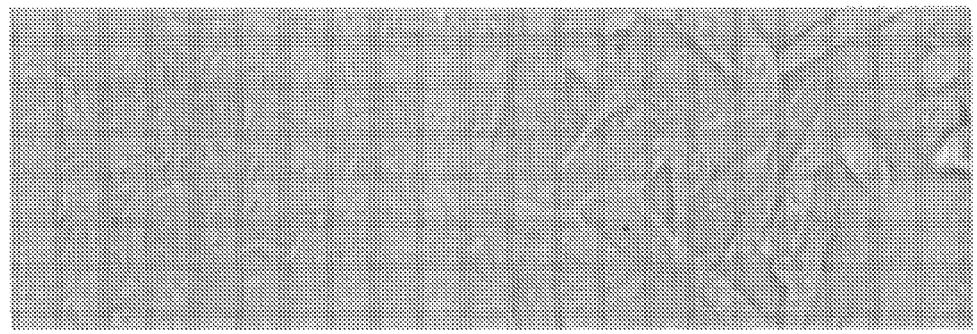
FIG. 1 is an illustration of untreated B16-F10 cells in McCoy's Media (100× on the left) and in PBS (200× on the right).

B16-F10 cells grow exponentially as adherent monolayers (FIG. 1), and require fluid renewal and/or sub-culturing every 2 to 3 days using 0.25% trypsin-EDTA (Sigma Chemical Co., St. Louis, Mo.) for detachment.

Cells were prepared for experiments by first harvesting by trypsinization and then washing 3 times by centrifugation. Cells were centrifuged (5810R, Eppendorf, Westbury, N.Y.) at 220×g for 5 minutes at 37° C. and resuspended in approximately 2.5 ml of PBS for each wash. A sample of cells was then diluted in 0.9% sodium chloride (APP, Schaumburg, Ill.) and 0.4% trypan blue stain (Cellgro Mediatech, Inc.). Trypan blue is an indicator in which the membranes of non-viable cells are penetrated and can be distinguished from the viable cells. Using a hemacytometer (Hausser Scientific, Horsham, Pa.), the viable and nonviable cells were counted. The number of cells per milliliter was computed by multiplying the number of cells counted per square millimeter×the dilution (when used)×10,000 (conversion factor). Only those cultures that resulted in 80% to 100% viability were used for experimentation.

Experiments were conducted using 48-well polystyrene tissue culture plates (BD Falcon. Franklin Lakes, N.J.). Each well held approximately 1.4 ml of liquid with a surface area of 0.75 $cm^2$. The depth and diameter of each well was 18 mm and 10 mm, respectively.

It was found that pre-treatment of the wells with a 0.1% gelatin (Acros, N.J., USA; Geel, Belgium) film coat reduced loosening of the cells after electrical stimulation. Under aseptic conditions, 150 µl of the sterile gelatin solution was added to each well and let stand for 1 hour. The gelatin was then aspirated from each of the wells and air dried for 5 minutes. 500 µl of McCoy's Media was added to the treated wells in addition to 7.5×10$^4$ viable cells and incubated at 37° C. for 18 hours before treatment.

Electrode:

Gilbert et al. designed and compared several innovative electrodes for use in electrochemotherapy treatment of murine B16 melanoma tumors. They found that a 6-needle array was the most successful when tested in vivo, measured statistically by a 97.1% complete response rate.

Figure 2:
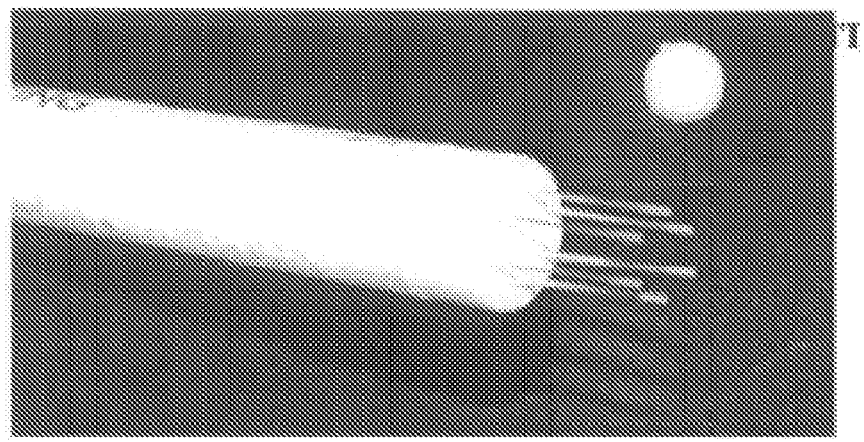
FIG. 2 is an illustration of an exemplary 6-needle electrode probe design in accordance with the present invention.

The electrode shown in FIG. 2 was specially designed for all experimentation in these studies and was similar to the design mentioned above. The electrode consisted of 6 stainless steel electrodes, equally spaced at 60° intervals around a 0.7 cm diameter circle. The needles extended 1.8 cm from the electrode body to fit precisely in the wells in order to set flush against the treatment/cell growth surface.

Figure 3:
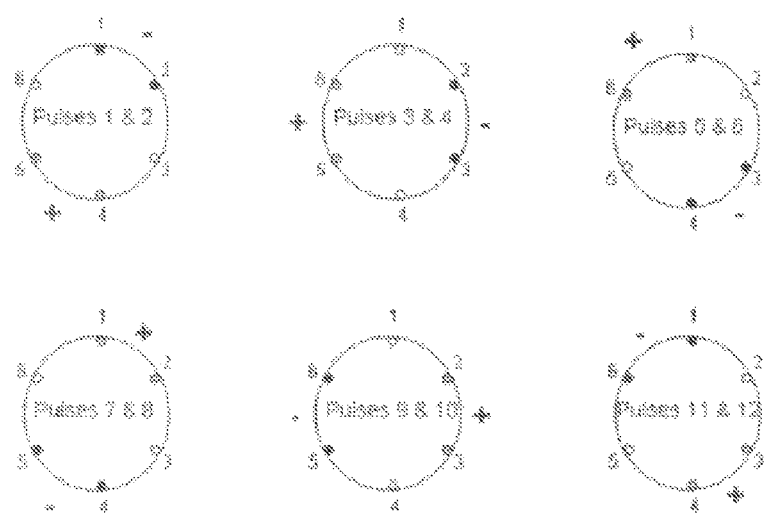
FIG. 3 is an illustration of a 6-needle pulsing sequence used for energizing cells in accordance with the present invention.

Cells in each well were treated with a total of 12 DC pulses. FIG. 3 illustrates the sequence pattern used to energize specific needles, where each small circle represents the location of each needle. Pulses were directed to each needle by a rotary switch. Needles 1 & 2 were negative (represented as dark circles) for the first two consecutive pulses, whereas opposing needles 4 & 5 (represented as lightly shaded circles) were positive. This pattern was repeated for the next two pulses except the pattern was rotated one-needle clockwise. This clockwise rotation preceded each set of two pulses and was repeated until 12 pulses were delivered. This sequence was designed to treat 360° of the cell growth surface.

Testing Conditions & Experimental Protocol:

A hot water bath (Isotemp 105, Fisher Scientific, Hampton, N.H.) was used during the treatment of the cultures to maintain cell viability and was set at 50° C. A sheet of Plexiglas was cut to fit over the water bath and was used as a surface for maintaining an approximate temperature of 37° C. All solutions used were allowed to reach room temperature (~22° C.) to prevent thermal shock to the cells.

The absolute amplitude for the DC pulse generator (Transfector 800; BTX, Inc., San Diego, Calif.) ranged from 0 to 970

V. which corresponds to electric field intensities delivered between 0 to 1385 V/cm. The pulse width was set within optimal conditions at 99 μsec (maximum). Using short electrical pulses for cellular manipulation has the advantage of resulting in negligible thermal heating.

Figure 4:
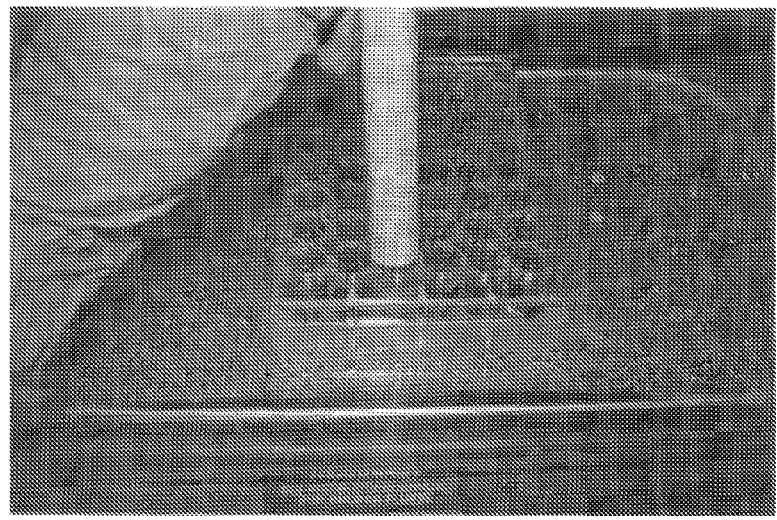
FIG. 4 is a photograph illustrating the electrical treatment in accordance with the present invention.

Each set of treatment conditions was tested in triplicate wells. Eighteen hours after seeding plates, each well was treated individually by aspirating the media, and quickly adding 150 μl of solution. This was just enough volume to coat the bottom of the well. For those conditions that required electric current, the electrode was placed down in the well so that the prongs set flush on the bottom to minimize any movement of the electrode (FIG. 4). Electrical current was then applied in the manner previously described.

After application of the pulses, cells were incubated for 1 hour at 37° C. This time allowed membrane resealing before the cells were carefully washed with 500 μl aliquots of PBS three times. Liquid from each wash was carefully and thoroughly aspirated. Then, each well was filled with 500 μl of PBS.

The presence of delivered calcein was observed under the microscope with the aid of a fluorescence microscope. A 0.9% sodium dodecyl sulfate (SDS) solution was then used to lyse the cells after the completion of the washing. SDS is a detergent that dissolves hydrophobic molecules. Therefore, when cells are incubated with an SDS solution, the membrane proteins and lipids denature and solubilize. 250 μl of the SDS solution was added to each of the wells containing PBS to yield a final concentration of 0.3%.

The contents of each well were transferred to a 5 ml FACS tube (BD Falcon). An additional 500 μl of PBS was added to each tube to increase sample volume. All samples were then centrifuged at 220×g for 5 minutes at 37° C.

Fluorescence Measurement:

Individual readings of each sample were taken using a fluorescence spectrometer (Perkin-Elmer LS-3B, Oakbrook. Ill.). The optimal excitation and emission wavelengths for calcein were found to be 488 and 515, respectively. The readings were made in a 1 cm$^2$ quartz cuvette, using a sample volume of 1 ml.

Membrane Recovery:

The membrane integrity of the cells after electroporation treatment is an essential factor for determining the applications in which this procedure will be utilized. It is typically desired to preserve, as much as possible, the original cellular structures of these living membranes in order to obtain optimal post-treatment results. As mentioned earlier, cellular membranes can undergo REB in which the biological structures will eventually return to their normal state. Twenty four hours post-treatment, the fate of the cells can typically he determined. For the purpose of this study, optimal testing conditions were used to treat B16F10 cells to conclude the extent of reversible permeation.

Figure 5:
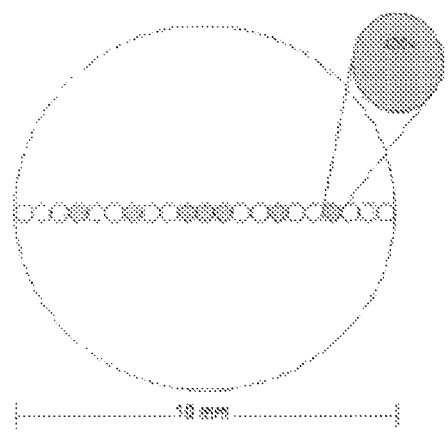
FIG. 5 is a diagrammatic view of the fields of view for one well at 400× magnification in accordance with the present invention, wherein the shaded circles represent the fields of view selected for counting.

Due to the large surface area of the wells, the cells were physically counted by observing 7 out of 21 fields of view along the horizontal diameter of each well at a magnification of 400× (see FIG. 5). The recovery of the membranes after exposure to each treating condition was expressed as a percentage of live cells remaining after each hour.

In order to distinguish the viable cells from the dead, a 0.4% trypan blue solution in PBS was used. 150 μl of the solution was added to each well for 1 minute, and then the cells were counted using the described method. Each test condition was studied at 1 hour intervals ranging from 1 hour to 4 hours. In addition, membrane recovery was examined 24 hours post treatment.

pH Measurements:

The three concentrations of ASA, SA, and AA had pH values that were determined. The pH measurements were made using a pH meter (Colloidal Dynamics, AZR2, Sydney, Australia), which was calibrated using 3 solutions with known pH values. The pH values of each solution were 4.7, and 10.

Statistical Methods:

To determine the statistical relevance of the data, a criterion for considering the mean data of one treatment condition as more successful than another had to be established. The null hypothesis used was that no change took place when considering one set of treatment parameters over another, and the alternative hypothesis used was that a significant change took place that resulted in different mean fluorescence values. The method used to test the null hypothesis was a two-tailed paired sample t test, with a level of significance of $\alpha=0.05$. If the computed t-score was in between the critical values, then the null hypothesis would be accepted, whereas if the t-score was a value that lied outside of the critical value parameters, there would be significant evidence to allow for a conclusion that the treatments differed in their effectiveness.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of delivery of a desired substance across a cell membrane comprising:
    contacting the cell membrane with a composition which permeabilizes the cell membrane, wherein the composition further comprises
    the desired substance; and
    acetylsalicylic acid having a pH of less than 5.4 and a concentration greater than 5 mM;
    whereby the cell membrane recovers membrane integrity after the desired substance has entered the cell.

2. The method according to claim 1 further comprising the step of applying an electric field to the contacted membrane to electroporate the membrane.

3. The method according to claim 1 wherein the concentration of acetylsalicylic acid is about 10 mM.

4. The method according to claim 3 further comprising the step of applying an electric field to the contacted membrane to electroporate the membrane.

5. The method according to claim 4 wherein the applied electric field is between about 500V/cm and about 1000 V/cm.

6. A method of delivery of a desired substance across a cell membrane comprising:
    contacting the membrane with a composition which permeabilizes the cell membrane, wherein the composition further comprises the desired substance; and acetic acid having a pH of less than 5.36 and a concentration of about 0.15%;

whereby the cell membrane recovers membrane integrity after the desired substance has entered the cell.

7. The method according to claim 6 further comprising the step of applying an electric field to the contacted membrane to electroporate the membrane.

8. The method according to claim 6 wherein the pH of acetic acid is about 4.4.

9. The method according to claim 8 further comprising the step of applying an electric field to the contacted membrane to electroporate the membrane.

10. The method according to claim 9 wherein the applied electric field is between about 500V/cm and about 1000 V/cm.

11. A method of permeabilizing a cell membrane to facilitate entry of a desired molecule into a cell comprising:

contacting the cell membrane with a permeabilizing agent selected from the group consisting of acetylsalicylic acid and acetic acid; and contacting the cell membrane with a desired substance;

wherein acetylsalicylic acid has a pH of less than 5.4 and a concentration greater than 5 mM and acetic acid has a pH of less than 5.36 and a concentration of about 0.15%;

whereby the cell membrane recovers membrane integrity after the desired substance has entered the cell.

12. The method according to claim 11 further comprising the step of applying an electric field to the contacted membrane to electroporate the membrane.

13. The method according to claim 12 wherein the applied electric field is between about 500V/cm and about 1000 V/cm.

14. The method according to claim 12 wherein the electric field is generated using short electrical pulses.

15. The method of claim 1 wherein the pH of acetylsalicylic acid is about 4.4.

16. The method of claim 11 wherein the pH of acetylsalicylic acid and acetic acid is 4.4.

17. The method of claim 11 wherein the concentration of acetylsalicylic acid is about 10 mM.

18. The method of claim 11 wherein the cell membrane is contacted concomitantly with the permeabilizing agent and the desired substance.

19. The method of claim 11 wherein the cell membrane is contacted with the permeabilizing agent first and subsequently contacted with the desired substance.

* * * * *